(12) United States Patent
Nikam

(10) Patent No.: US 6,395,930 B1
(45) Date of Patent: May 28, 2002

(54) QUENCHING REAGENTS FOR SOLUTION PHASE SYNTHESIS

(75) Inventor: Sham Nikam, Ann Arbor, MI (US)

(73) Assignee: Warner Lambert, Ann Arbor, MI (US)

( * ) Notice: Subject to any disclaimer, the term of this patent is extended or adjusted under 35 U.S.C. 154(b) by 0 days.

(21) Appl. No.: 09/577,393

(22) Filed: May 25, 2000

Related U.S. Application Data

(62) Division of application No. 09/157,869, filed on Sep. 21, 1998, now Pat. No. 6,121,488.

(51) Int. Cl.$^7$ .............................................. C07C 321/02
(52) U.S. Cl. .......................... 562/556; 562/11; 562/12; 562/30; 562/101; 562/432; 562/442; 562/444; 562/473; 562/565; 562/556; 562/504; 560/37; 560/122; 560/147; 560/152
(58) Field of Search .................... 562/432, 444, 562/442, 473, 565, 11, 512, 12, 30, 101, 504, 556; 560/37, 122, 147, 152

(56) References Cited

FOREIGN PATENT DOCUMENTS

| DE | 19711724 | * 11/1997 |
| JP | 6-184086 | 7/1994 |

OTHER PUBLICATIONS

Alexandratos, S. et al., "Polymer–Supported Reagents: Application to Separation Science", *Ind. Eng. Chem. Res.*, vol. 35, No. 3, pp. 635–644 (1996).
Booth, R. et al., "Solid–Supported Reagent Strategies for Rapid Purification of Combinatorial Synthesis Products", *Acc. Chem. Res.*, vol. 32, No. 1, pp. 18–26 (1999).
Cheng, S. et al., "Novel Solution Phase Strategy for the Synthesis of Chemical Libraries Containing Small Organic Molecules", *J. Am. Chem. Soc.*, vol. 118, No. 11, pp. 2567–2573 (1996).
Flynn, D. et al., "Polymer–Assisted Solution Phase (PASP) Chemical Library Synthesis", *Med. Chem. Res.*, vol. 8, No. 4/5, pp. 219–243 (1998).
Flynn, D. et al., "Recent Advances in Polymer–Assisted Solution–Phase Chemical Library Synthesis and Purification", *Drug Discovery and Development*, vol. 1, No. 1, pp. 41–50 (1998).
Fruchtel, J. et al., "Organic Chemistry on Solid Supports", *Angew. Chem. Int. Ed. Engl.*, vol. 35, pp. 17–42 (1996).
Gayo, L. et al., "Ion–Exchange Resins for Solution Phase Parallel Synthesis of Chemical Libraries", *Tetrahedron Letters*, vol. 38, No. 4, pp. 513–516 (1997).
Gordon, E. et al., "Applications of Combinatorial Technologies to Drug Discovery. 2. Combinatorial Organic Synthesis, Library Screening Strategies, and Future Directions", *Journal of Medicinal Chemistry*, vol. 37, No. 10, pp. 1385–1401 (May 13, 1994).
Hermkens, P. et al., "Solid–Phase Organic Reactions: A Review of the Recent Literature", *Tetrahedron Report Number 394*, vol. 52, No. 13, pp. 4527–4554 (1996).
Kaldor, S. et al., "Use of Solid Supported Nucleophiles and Electrophiles for the Purification of Non–Peptide Small Molecule Libraries", *Tetrahedron Letters*, vol. 37, No. 40, pp. 7193–7196 (1996).
Nikam, S. et al., "Novel Quenchers for Solution Phase Parallel Synthesis", *Tetrahedron Letters*, vol. 39, pp. 1121–1124 (1998).
Rubinstein, M. et al., "The Use of a Light–Sensitive Phosphate Protecting Group for Some Mononucleotide Syntheses", *Tetrahedron Letters*, No. 17, pp. 1445–1448 (1975).
Sherrington, D., "Polymer–Supported Systems: Towards Clean Chemistry?", *Chemistry &Industry*, pp. 15–19 (Jan. 7, 1991).
Suto, M., "Developments in Solution–Phase Combinatorial Chemistry", *Drug Discovery & Development*, vol. 2, No. 4, pp. 377–384 (1999).
Terrett, N. et al., "Combinatorial Synthesis—The Design of Compound Libraries and their Application to Drug Discovery", *Tetrahedron*, vol. 51, No. 30, pp. 8135–8173 (1995).
Thompson, L. et al., "Synthesis and Applications of Small Molecule Libraries", *Chem. Rev.*, vol. 96, pp. 555–600 (1996).
Uhrich, K. et al., "The Solid–Phase Synthesis of Dendritic Polyamides", *Polymer Bulletin*, vol. 25, pp. 551–558 (1991).

* cited by examiner

Primary Examiner—Shailendra Kumar
(74) Attorney, Agent, or Firm—Merchant & Gould P.C.

(57) ABSTRACT

A method for enhancing the purity of a desired compound comprising:

Step (a) treating a crude reaction product which contains at least one desired compound, unreacted starting materials and/or byproducts with at least one bifunctional quenching agent that is capable of selective covalent reaction with unwanted byproducts, or excess reagents;

Step (b) allowing the quenching agent to covalently react with unreacted starting materials and/or byproducts to afford a derivatized compound of the quenching agent: and Step (c) isolating the desired compound is described as well as novel quenching agents and methods for their use in the rapid purification of synthetic intermediates and products in synthesis, combinatorial chemistry, and automated organic synthesis.

3 Claims, No Drawings

QUENCHING REAGENTS FOR SOLUTION PHASE SYNTHESIS

This is a Divisional of application Ser. No. 09/157,869, filed Sep. 21, 1998, now U.S. Pat. No. 6,121,488, which is a continuation of provisional application Ser. No. 60/059,860, filed on Sep. 24, 1997, which application(s) are herein incorporated by reference.

BACKGROUND OF THE INVENTION

The present invention relates to novel quenching reagents and to methods for their use in the purification of synthetic intermediates and products in the practice of organic synthesis, combinatorial chemistry, and automated organic synthesis.

Combinatorial chemistry and automated organic synthesis have proven to be highly effective means for the generation of multiplicities of novel molecules known as libraries. As the size of such a library grows, so does the likelihood that it will contain individual molecules with useful biological activities which may be employed in the treatment of human, animal, and plant diseases. Research organizations that can prepare and screen a large number of diverse compounds efficiently, have an increased likelihood of discovering and optimizing new products. For recent reviews in the use of combinatorial chemistry in pharmaceutical discovery see Gallop M. A., et al., *J. Med. Chem.*, 1994;37:1233, Gordon E. M., et al., ibid., 1994;37:1385, Terret N. K., et al., *Tetrahedron*, 1995;51:8135, and Ellman J. A., et al., *Chem. Rev.*, 1996;96:555.

In the practice of organic synthesis, the most time consuming element is typically the purification of the desired product following each synthetic transformation. Traditionally, automated organic synthesis and combinatorial chemistry have relied on a number of methods to reduce the amount of time and effort devoted to purification. Such methods include water soluble reagents, polymer-supported reagents, and polymer-supported synthesis. Water soluble reagents and byproducts derived therefrom have the advantage of being easily removed by partitioning the crude reaction mixture between water (which dissolves the reagent and associated byproducts) and an organic solvent (which dissolves the desired product). Separation of the organic layer gives a purified form of the product relative to the crude reaction mixture. An example of a water soluble reagent is N-ethyl-N'-dimethylaminopropylcarbodiimide (EDC). EDC is reagent that is used in the coupling of carboxylic acids and amines to form amide bonds. EDC and the corresponding urea produced during the course of the reaction (N-ethyl-N'-dimethylaminopropylurea) are both soluble in water at low pH and can thus be washed away into an acidic water layer. The use of EDC greatly simplifies purification of the amide product relative to other carbodiimides such as N,N'-dicyclohexylcarbodiimide (DCC) which are not water soluble. Polymer-supported reagents and byproducts derived therefrom are likewise easily separated by filtration of the polymeric materials from a crude reaction mixture. An example of a polymer-supported reagent is poly(styrene-divinylbenzene)-supported triphenylphosphine which may be used in Wittig olefination and Mitsunobu reactions. The byproduct of this transformation, polymer-supported triphenylphosphine oxide, is easily removed by filtration which simplifies purification greatly compared to the solution phase reagent. The use of triphenylphosphine in solution phase Wittig reactions gives triphenylphosphine oxide as a byproduct which is difficult to completely remove except by time consuming chromatography or repeated crystallization. Polymer-supported synthesis minimizes time spent on purifications by attaching a starting material to a polymer. Subsequent synthetic transformations are carried out in such a manner that desired reactions are driven to completion on the polymer-supported material and excess reagents and byproducts in solution are subsequently removed by filtering the polymer and rinsing with solvent(s). At the end of the synthesis, the desired product is chemically cleaved from the polymer. The resulting product is typically obtained in greater purity than would be possible if all of the steps were carried out in solution with no chromatography or crystallization of synthetic intermediates. Purification in a multistep synthesis is thus largely reduced to a number of filtrations, although a single purification of the final product by conventional means is often necessary to remove byproducts resulting from the resin cleavage step. Thus, water soluble reagents, polymer-supported reagents, and polymer-supported synthesis each provide increased efficiency reducing purification to mechanically simple liquid-liquid and liquid-solid separation methods which are easy to automate.

The increased simplicity and efficiency which allow automation of organic synthesis using the methods described above comes at the price of increased reagent cost and/or substantial synthesis development time. Water soluble reagents and polymer-supported reagents must be customized for each type of synthetic transformation. The time necessary to optimize a particular reagent significantly increases its cost. Consequently, EDC is more expensive than DCC and polystyrene-supported triphenylphosphine is more expensive than triphenylphosphine. Polymer-supported syntheses traditionally require longer development time than solution phase due to the limitations imposed by the method. One must choose the optimum polymer, develop a linking strategy which can be reversed at the end of the synthesis and find successful conditions for each reaction without many of the conventional spectral and chromatographic analysis tools that are available to solution phase synthesis. Thus, at the current state of the art, much of the time/cost saved by increasing the efficiency of purifications via the above methods is lost to increased reagent costs and/or synthetic development time.

Polymer-supported reagents have been extensively reviewed in the literature. The following citation is representative of the current state of this art: Sherrington D. C., *Chem. Ind.*, (London) 1991;1:15–19.

Solid-supported synthesis has been extensively reviewed in the literature. The following two citations are representative of the current state of this art: Früchtel J. S. and Jung G., *Angew. Chem. Int. Ed. Engl.*, 1996;35:17–42, Thompson L. A. and Ellman J. A., *Chem. Rev.*, 1996;96:555–600.

A purification process known as covalent chromatography has been described in the scientific literature. Using covalent chromatography a desired material is isolated from a complex mixture by selective reaction with a polymeric reagent, followed by filtration, and rinsing. The desired material is then liberated from the polymer by a chemical cleavage. Typically this process is applied to proteins and other macromolecules as a way of isolating them from complex mixtures of cellular components. This technique has also been applied in the separation of low molecular weight allergens from plant oils as described by Cheminat A., et al., in *Tetr. Lett.*, 1990;617–619. Covalent chromatography differs from the instant invention in that the polymeric materials used must be both capable of covalently reacting with a desired material in a solution containing impurities and capable of subsequent cleavage of said covalent bond during the retrieval of the desired material. Polymer-supported quench methods of the present invention rely on chemically robust and ideally irreversible attachment of undesired materials that are found in the crude product of an organic reaction to a polymeric support, leaving the desired product in solution.

Polymeric reagents have been employed during the course of a reaction to enhance yield of the desired product by minimizing side reactions as described by Rubenstein M. and Patchornik A., *Tetr. Lett.*, 1975;1445–8, but this use of a polymeric reagent does not eliminate the need for conventional purification of the desired product.

Polymeric reagents which selectively remove metal ions from solutions by chelation have been described but this use of a polymeric reagent in purification does not involve formation of covalent bonds. For a review of the current state of this art see Alexandratos S. D. and Crick D. W., *Ind. Eng. Chem. Res.*, 1996;35:635–44.

The synthesis of dendritic polyamides on polymeric supports has been described by Ulrich K. E., et al., *Polymer Bul.*, 1991;25:551–8. As synthetic intermediates of the synthesis, polymer-supported dendritic polyamines are described which, by virtue of the fact that they contain an easily cleaved linker, are structurally distinct from those of the present invention which contain chemically robust linkers.

Solution-phase parallel synthesis is an excellent way to form large libraries of small molecules. This is a logical extension of solid phase organic synthesis (SPOS) which has a few limitations in terms of selection of resins and an appropriate handle to hook up the resin on the substrate (Thompson L. A. and Ellman J. A., *Chem. Rev.*, 1996;96:555; Hermkens P. H. H., Ottenheijm H. C. J., and Rees D., *Tetrahedron*, 1996;52:4527). Additionally, SPOS may not be compatible to a variety of reagent types and in future will need other complementary solution phase methods to give pure compounds in multi-gram quantities in good yields. Earlier, a few reports have appeared where solid phase quenchers in the form of reagents on the solid-phase (Kaldor S. W., Siegel M. G., Frita J. E., Dressman B. A., and Hahn P. J., *Tetrahedron Lett.*, 1996;37:7193) or ion exchange resins (Gayo L. M. and Suto M. J., *Tetrahedron Let.*, 1997;38:513) have been used for quenching reactions to eliminate the reactive components in the reaction. Boger and his coworkers (Cheng S., Comer D. D., Williams J. P., Myers P. L., and Boger D. L., *J. Am. Chem. Soc.*, 1996;118:2567) have also reported an excellent protocol for multiple step solution phase parallel synthesis to synthesize final compounds in good purity and quantities.

The aforementioned references do not describe or suggest the quench reagents disclosed herein, nor do they teach the purification utility of a quench reagent in the practice of organic synthesis, of automated organic synthesis and combinatorial chemistry as described in the present invention.

Thus, we have surprisingly and unexpectedly found that one or more reagents can be added at the conclusion of an organic reaction to covalently react with excess reagents and/or unwanted byproducts. The impurities are then easily removed by conventional separation techniques leaving a solution of the desired synthetic intermediate or product which is enhanced in purity relative to the crude reaction mixture. Purification by quench is mechanically simple and rapid compared to conventional means of purification such as column chromatography, distillation or crystallization. This means of purification is readily applied to large variety of organic reactions and is amenable to both manual and automated organic synthesis environments. Hence, it is of tremendous value in the preparation of large libraries of organic molecules by automated parallel synthesis and by automated or manual combinatorial synthesis.

SUMMARY OF THE INVENTION

Accordingly, a first aspect of the present invention is a method for enhancing the purity of a desired compound which comprises:

Step (a) treating a crude reaction product which contains at least one desired compound, unreacted starting materials and/or byproducts with at least one compound of Formula I

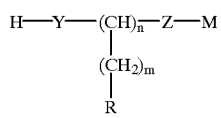

I wherein
Y is

wherein
R³ is
hydrogen,
alkyl,
aminoalkyl,
alkylaminoalkyl,
dialkylaminoalkyl,
carboxyalkylaminoalkyl,
phosphonoalkylaminoalkyl,
sulfonylalkylaminoalkyl,
hydroxyalkyl,
thioalkyl,
arylalkyl,
cycloalkyl,
heterocycloalkyl, or
aryl,
—S—, or
—O—;
n is an integer of from 1 to 10;
m is zero or an integer of from 1 to 6;
R is
hydrogen,
alkyl,
alkenyl,
alkynyl,
cycloalkyl,
aryl,
heteroaryl,

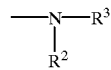

wherein
R² and R³ are each the same or different and each is
hydrogen,
alkyl, cycloalkyl,
aryl, or
heteroaryl,
—$OR^2$, wherein $R^2$ is as defined above,
—$SR^2$, wherein $R^2$ is as defined above,

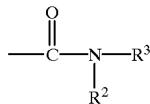

wherein $R^2$ and $R^3$ are each the same or different and each is as defined above for $R^2$ and $R^3$,

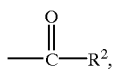

wherein $R^2$ is as defined above,

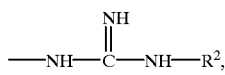

wherein $R^2$ is as defined above, or

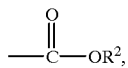

wherein $R^2$ is as defined above;

Z is

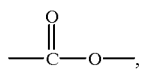

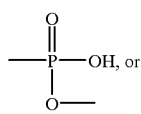

or

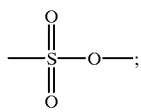

and

M is an alkali metal or alkaline earth metal that is capable of selective covalent reaction with unwanted byproducts, or excess reagents;

Step (b) allowing a compound of Formula I to covalently react with unreacted starting materials and/or byproducts to afford a derivatized reagent of Formula II

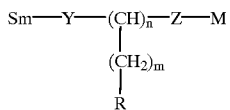

wherein Sm is unreacted starting material and/or byproduct and Y, n, m, R, Z, and M are as defined above; and Step (c) isolating the desired compound.

A second aspect of the present invention is a compound of Formula Ia

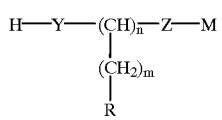

wherein
Y is

wherein $R^{3a}$ is —$(CH_2)_p$—X
wherein p is an integer of 2 to 6 and

X is $Y^a$—$(CH_2)_q$—$Z^a$ wherein $Y^a$ is O, or S,
q is an integer of 1 to 6, and
$Z^a$ is —$CO_2R^4$ wherein $R^4$ is hydrogen, alkyl, or arylalkyl,
—$PO_3HR^4$ wherein $R^4$ is as defined above, or
—$SO_2R^5$ wherein $R^5$ is hydroxy,
alkoxyl,
aryloxy,

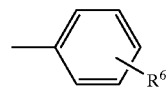

wherein $R^6$ is —$CO_2R^4$
wherein $R^4$ is as defined above, —$PO_3HR_4$
wherein $R^4$ is as defined above, or —$SO_2R^5$
wherein $R^5$ is as defined above, or

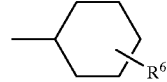

wherein $R^6$ is as defined above;
n is an integer of from 1 to 10,
m is zero or an integer of from 1 to 6;
R is
hydrogen,
alkyl,
alkenyl,
alkynyl,
cycloalkyl,
aryl, heteroaryl,

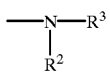

wherein
$R^2$ and $R^3$ are each the same or different and each is
  hydrogen,
  alkyl,
  cycloalkyl,
  aryl, or
  heteroaryl,
—$OR^2$, wherein $R^2$ is as defined above,
—$SR^2$, wherein $R^2$ is as defined above,

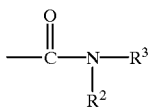

wherein $R^2$ and $R^3$ are each the same or different and
each is as defined above for $R^2$ and $R^3$,

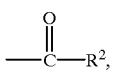

wherein $R^2$ is as defined above,

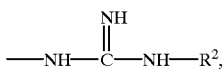

wherein $R^2$ defined above, or

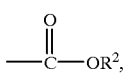

wherein $R^2$ is as defined above;
Z is

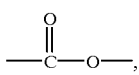

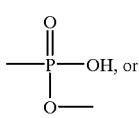

or

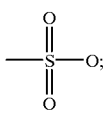

and
M is an alkali metal or alkaline earth metal, which is useful as a quenching reagent in the process of the present invention.

DETAILED DESCRIPTION OF THE INVENTION

In the compounds of Formula I, the term "alkyl" means a straight or branched hydrocarbon radical having from 1 to 12 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, dodecyl, and the like.

The terms "aminoalkyl", "hydroxyalkyl", and "thioalkyl" are respectively $H_2N$-alkyl, HO-alkyl, and HS-alkyl as defined above for alkyl.

The terms "alkylaminoalkyl", "dialkylaminoalkyl", "carboxyalkylaminoalkyl", "phosphonoalkylaminoalkyl", and "sulfonylalkylaminoalkyl" are respectively alkyl-NH-alkyl, (alkyl)$_2$ N-alkyl, $HO_2C$-alkyl-NH-alkyl, $(HO)_2$ PO-alkyl-NH-alkyl, and $SO_2$-alkyl-NH-alkyl as defined above for alkyl.

The term "alkenyl" means a straight or branched unsaturated hydrocarbon radical having from 2 to 12 carbon atoms and includes, for example, ethenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, 1-undecenyl, 1-dodecenyl, and the like.

The term "alkynyl" means a straight or branched triple bonded unsaturated hydrocarbon radical having from 2 to 12 carbon atoms and includes, for example, ethynyl, 2-propynyl, 1-butynyl, 2-butynyl, 3-butynyl, 1-pentynyl, 3-pentynyl, 1-hexynyl, 2-hexynyl, 3-hexynyl, 3-heptynyl, 1-octynyl, 2-octynyl, 1-nonynyl, 2-nonynyl, 3-nonynyl, 4-nonynyl, 1-decynyl, 2-decynyl, 2-undecynyl, 3-undecynyl, 3-dodecynyl, and the like.

The term "cycloalkyl" means a saturated hydrocarbon ring which contains from 3 to 12 carbon atoms, for example, cyclopropyl, cyclobutyl, cyclopentyl, cyclohexyl, adamantyl, and the like.

The term "cycloalkylalkyl" means a saturated hydrocarbon ring attached to an alkyl group wherein alkyl is as defined above. The saturated hydrocarbon ring contains from 3 to 12 carbon atoms. Examples of such are cyclopropylmethyl, cyclopentylmethyl, cyclohexylmethyl, adamantylmethyl and the like.

The terms "alkoxy" and "thioalkoxy" are O-alkyl or S-alkyl as defined above for alkyl.

The terms "alkoxyalkyl" and "thioalkoxyalkyl" are O-alkylalkyl or S-alkylalkyl as defined above for alkyl.

The term "aryl" means an aromatic radical which is a phenyl group, a benzyl group, a naphthyl group, a biphenyl group, a pyrenyl group, an anthracenyl group, 3,3-diphenylalanyl, 10,11-dihydro-5H-dibenzo[a,d]-(cyclohepten-5-yl)glycyl, or a fluorenyl group and the like, unsubstituted or substituted by 1 to 4 substituents selected from alkyl as defined above, alkoxy as defined above, thioalkoxy as defined above, hydroxy, thiol, nitro, halogen, amino,

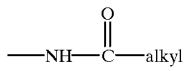

wherein alkyl is as defined above,

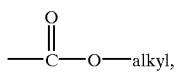

wherein alkyl is as defined above,

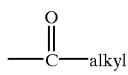

wherein alkyl is as defined above, or aryl.

The term "arylalkyl" means an aromatic radical attached to an alkyl radical wherein aryl and alkyl are as defined above for example benzyl, fluorenylmethyl and the like.

The term "aryloxy" means O-aryl as defined above for aryl.

The term "heteroaryl" means a heteroaromatic radical which is 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, or 2-, 4-, 5-, 6-, or -7-benzoxazolyl, 2-, 4-, 5-, 6-, or 7-benzimidazolyl, 2-, 4-, 5-, 6-, or 7-benzothiazolyl, unsubstituted or substituted by 1 to 2 substituents selected from alkyl as defined above, aryl as defined above, alkoxy as defined above, thioalkoxy as defined above, hydroxy, thiol, nitro, halogen, formyl, amino,

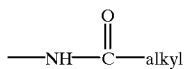

wherein alkyl is as defined above,

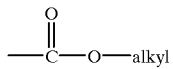

wherein alkyl is as defined above,

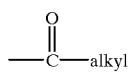

wherein alkyl is as defined above or phenyl.

The term "heterocycloalkyl" means 2- or 3-tetrahydrothieno, 2- or 3-tetrahydrofurano, 2- or 3-pyrrolidino, 2-, 4-, or 5-thiazolidino, 2-, 4-, or 5-oxazolidino, 2-, 3-, or 4-piperidino, N-morpholinyl or N-thiamorpholinyl.

"Halogen" (Halo) is fluorine, chlorine, bromine, or iodine.

The term "haloalkyl" is as defined above for halo and alkyl.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, and the like.

The term "byproduct" means an undesirable product of a reaction which comprises at least five mole percent of the crude product. Isomers, enantiomers, and diastereomers of the desired product are not considered to be byproducts within the scope of this invention.

The term "crude reaction product" means the result of a chemical reaction before any purification. Synonymous with crude product and crude reaction mixture.

The term "enhancing purity" means: A) For a single desired compound, enhancing purity means the process of removing excess or unreacted starting reagents to the limit of detection by thin layer chromatography (TLC) or by $^1$H-NMR spectroscopy and/or reducing the content of any single byproduct to less than ten molar percent, exclusive of solvents; B) For a combinatorial mixture of desired compounds: The process of removing excess or unreacted starting reagents and/or reducing the content of a byproduct using a procedure that has been validated on crude reaction products of analogous single compounds.

The term "quenching reagent" means a molecule that covalently combines with a reactant to make it less reactive or a molecule that covalently combines with a byproduct.

The following table provides a list of abbreviations and definitions thereof used in the present invention.

| Abbreviation | Definition |
|---|---|
| Et | Ethyl |
| Me | Methyl |
| i-Pr | Isopropyl |
| TEA | Triethylamine |
| THF | Tetrahydrofuran |
| EtOAc | Ethyl acetate |
| DMF | N,N-Dimethylformamide |
| Mesyl | Methanesulfonyl |
| Tosyl | 4-Toluenesulfonyl |
| Triflyl | Trifluoromethanesulfonyl |
| KOH | Potassium hydroxide |
| $H_2O$ | Water |
| $BH_3$ | Borane |
| HCl | Hydrochloric acid |
| MeOH | Methanol |
| Cbz | Carbobenzyloxy |
| t-Bu | tertiary Butyl |
| Pd/C | Palladium on charcoal |
| $H_2$ | Hydrogen |
| $NaBH_3CN$ | Sodium cyanoborohydride |
| $CH_2Cl_2$ | Methylene dichloride |
| $CHCl_3$ | Chloroform |
| $SiO_2$ | Silicon dioxide (silica) |
| $MgSO_4$ | Magnesium sulfate |
| $CaCl_2$ | Calcium chloride |
| Psi | Pounds per square inch |
| $^1$H-NMR | Proton nuclear magnetic resonance spectroscopy |
| MS | Mass spectroscopy |

In the second aspect of the present invention, a preferred compound of Formula Ia is

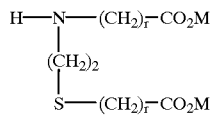

wherein r is an integer of from 1 to 4, and M is an alkali metal or alkaline earth metal.

In the second aspect of the present invention, another preferred compound of Formula Ia is

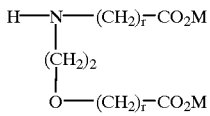

wherein r is an integer of from 1 to 4, and M is an alkali metal or alkaline earth metal.

In the second aspect of the present invention, another preferred compound of Formula Ia is

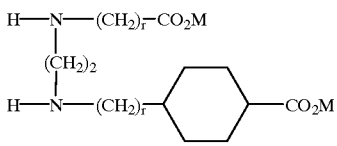

wherein r is an integer of from 1 to 4, and M is an alkali metal or alkaline earth metal.

In the second aspect of the present invention, another preferred compound of Formula Ia is

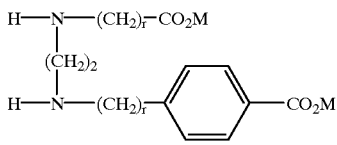

wherein r is an integer of from 1 to 4 and M is an alkali metal or alkaline earth metal.

Particularly valuable compounds of Formula Ia which are useful in the present process are selected from the group consisting of:

(2-Carboxymethylsulfanyl-ethylamino)-acetic acid;
3-[2-(Carboxymethyl-amino)-ethylsulfanyl]-propionic acid;
4-[2-(Carboxymethyl-amino)-ethylsulfanyl]-butyric acid;
5-[2-(Carboxymethyl-amino)-ethylsulfanyl]-pentanoic acid;
(2-(Carboxymethoxy-ethylamino)-acetic acid;
3-[2-(Carboxymethyl-amino)-ethoxy]-propionic acid;
4-[2-(Carboxymethyl-amino)-ethoxy]-butyric acid;
5-[2-(Carboxymethyl-amino)-ethoxy]-pentanoic acid;
4-{[2-(Carboxymethyl-amino)-ethylamino]-methyl}-cyclohexanecarboxylic acid;
4-{[2-(2-Carboxy-ethylamino)-ethylamino]-methyl}-cyclohexanecarboxylic acid;
4-{2-[2-(Carboxymethyl-amino)-ethylamino]-ethyl}-cyclohexanecarboxylic acid;
4-{2-[2-(2-Carboxy-ethylamino)-ethylamino]-ethyl}-cyclohexanecarboxylic acid;
4-{[2-(Carboxymethyl-amino)-ethylamino]-methyl}-benzoic acid;
4-{[2-(2-Carboxy-ethylamino)-ethylamino]-methyl}-benzoic acid;
4-{2-[2-(Carboxymethyl-amino)-ethylamino]-ethyl}-benzoic acid; and
4-{2-[2-(2-Carboxy-ethyl-amino)-ethylamino]-ethyl}-benzoic acid;
or an alkali metal or an alkaline earth metal salt thereof.

The method of the present invention in its first aspect is a novel process for purifying compounds. The method of the present invention in its first aspect is outlined in Scheme 1.

SCHEME 1

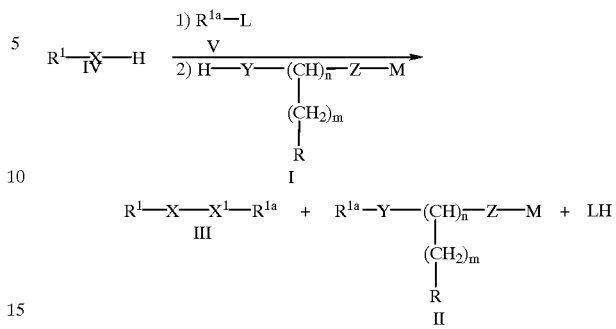

Thus, a compound of Formula III wherein $R^1$ and $R^{1a}$ are the same and are
alkyl,
haloalkyl,
aminoalkyl,
hydroxyalkyl,
thioalkyl,
alkoxyalkyl,
thioalkoxyalkyl,

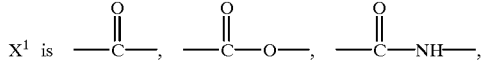

wherein $R^2$ and $R^{2a}$ are each the same or different and each is
alkyl,
aminoalkyl,
hydroxyalkyl,
thioalkyl,
arylalkyl,
cycloalkyl,
heterocycloalkyl, or
aryl;
X is —NH—; and $X^1$ is $-\underset{\underset{O}{\|}}{C}-$, $-\underset{\underset{O}{\|}}{C}-O-$, $-\underset{\underset{O}{\|}}{C}-NH-$, or

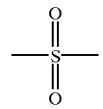

is prepared from a compound of Formula IV wherein $R^1$ and X are as defined above by treatment with a compound of Formula V wherein $R^{1a}$ is as defined above, and L is halogen,

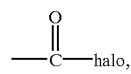

—N=C=O, tosyl, mesyl, triflyl and the like in a solvent such as, for example, THF, DMF and the like followed by subsequent quenching of the reaction with a compound of Formula I

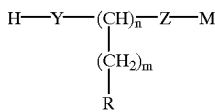

wherein
Y is

wherein
R³ is
  hydrogen,
  alkyl,
  aminoalkyl,
  alkylaminoalkyl,
  dialkylaminoalkyl,
  carboxyalkylaminoalkyl,
  phosphonoalkylaminoalkyl,
  sulfonylalkylaminoalkyl,
  hydroxyalkyl,
  thioalkyl,
  arylalkyl,
  cycloalkyl,
  heterocycloalkyl, or
  aryl,
  —S—, or
  —O—;
n is an integer of from 1 to 10;
m is zero or an integer of from 1 to 6;
R is
  hydrogen,
  alkyl,
  alkenyl,
  alkynyl,
  cycloalkyl,
  aryl,
  heteroaryl,

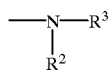

wherein
R² and R³ are each the same or different and each is
  hydrogen,
  cycloalkyl,
  aryl, or
  heteroaryl,
—OR², wherein R² is as defined above,
—SR², wherein R² is as defined above,

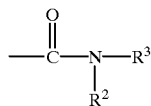

wherein R² and R³ are each the same or different and each is as defined above for R² and R³,

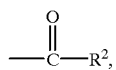

wherein R² is as defined above,

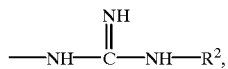

wherein R² is as defined above, or

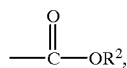

wherein R² is as defined above;
Z is

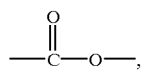

or

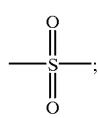

and
M is an alkali metal or alkaline earth metal, to afford a compound of Formula III wherein R¹ and R¹ᵃ are as defined above. The derivatized quench reagent of Formula II wherein R¹ᵃ, Y, n, m, Z, and M are as defined above is removed by aqueous extraction.

Preferred compounds of Formula I which are useful as novel quenching reagents in solution phase synthesis are selected from the group consisting of:

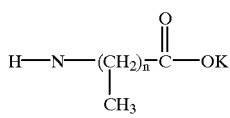

wherein n is an integer of from 1 to 10;

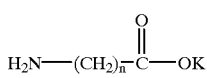

wherein n is an integer of from 1 to 10;

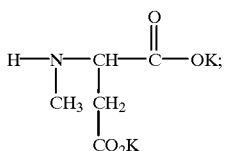

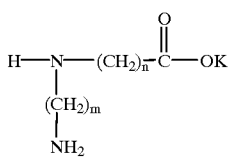

wherein n is an integer of from 1 to 10, and m is an integer of from 1 to 6;

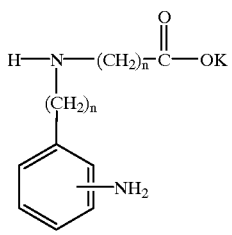

wherein n is an integer of from 1 to 10, and m is an integer of from 1 to 6;

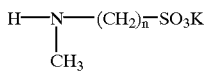

wherein n is an integer of from 1 to 10;

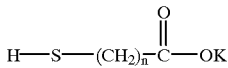

wherein n is an integer of from 1 to 10; and

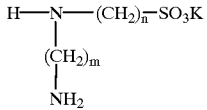

wherein n is an integer of from 1 to 10, and m is an integer of from 1 to 6.

Scheme 2 shows the reaction of N-benzylamine with an electrophile and the use of a most preferred compound of Formula I as a novel quencher in solution phase synthesis. Thus, potassium sarcosinate is used as the quenching agent to exploit the bifunctional, nature of this aminoacid. The amine end of the aminoacid is important for quenching the excess electrophile and the carboxylic acid end for solubilizing the impurity bound aminoacid in aqueous medium. Sarcosine has high nucleophilicity and basicity (amine functionality, pKa:10.01). The potassium salt is used due to increased solubility in organic solvents such as, for example, DMF, THF and the like. The potassium salt is prepared by mixing equimolar quantities of sarcosine and methanolic KOH. The solvent is evaporated, and the white solid is dried under vacuum (0.02 mm). After aqueous quench, no sarcosine or its derivatives are seen in $^1$H-NMR of the products. This methodology works when using large excess of electrophiles in the reaction which needs to be quenched with excess amounts of potassium sarcosinate. This is especially important when the amine or nucleophile needs to be conserved. Similarly, acid chlorides, sulfonyl chlorides, and isocyanates were completely consumed after potassium sarcosinate quench.

Thus, in a typical reaction, one equivalent of the amine is treated with an excess (>1.5 equivalents) of the electrophile such as, for example, an acid chloride, chloroformate, isocyanate, sulfonyl chloride and the like in the presence of a base such as, for example, triethylamine and the like in a solvent such as, for example, DMF, THF and the like. After stirring or shaking for about 4 hours, potassium sarcosinate (1 equivalent) is added to the reaction, and the mixture is stirred for an additional period of about 0.5 hour. Water is added under stirring and the product filtered or extracted with a solvent such as, for example, ethyl acetate and the like to afford the desired product. The reaction and purity of products can be monitored by $^1$H-NMR.

SCHEME 2

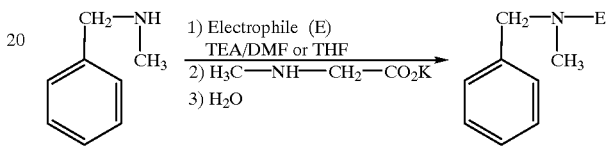

Of particular importance in the present invention is the use of the novel quenching reagents as an enabling technology for the preparation of libraries of organic molecules with potential biological activity. The quenching reagents of the present invention have utility in reducing purification time associated with automated parallel organic synthesis, manual combinatorial synthesis and automated combinatorial synthesis. Additionally, rapid purification by the quenching reagents of the present invention may be carried out using an automated synthesis apparatus such as, for example, the Diversomer® apparatus as described in U.S. Pat. No. 5,324,483 which is hereby incorporated by reference. Specific types of chemical transformations that benefit from this quench purification procedure include, but are not limited to, O- and N-acylation, O- and N-sulfonylation, O- and N-phosphonylation, O- and N-phosphonylation, C-, O-, N- and S-alkylation, condensation reactions, coupling reactions, cyclization reactions involving two or more components, and the like. Representative illustrations of specific cases wherein rapid purification of crude reaction mixtures is achieved with most preferred quenching reagents are described in Examples 1–3. Utility of the quenching reagents and methods described herein is not limited to the reactions described in these examples. On the contrary, the quenching reagents and methods described herein are broadly useful in these and many other organic reactions.

The novel compounds of the second aspect of the present invention can be prepared using procedures known in the art. For example, the novel compounds of Formula Ia can be prepared according to methodology disclosed in:

Williams, R. M. Synthesis of Optically active a-amino acids. 1–381 (1989), Pergamon Press;

Wirth, Thomas. New strategies to α-alkylate α-amino acids. *Angew. Chem., Int. Ed. Engl.,* 1997;36(3):225–227;

Sewald, N. Stereoselective synthesis of β-amino acids via conjugate addition of nitrogen nucleophiles to α,β-unsaturated esters. *Recent advances. Amino Acids,* 1996;11(34);397408;

Hlavacek, J.; Marcova, R.; Jezek, R.; Slaninova, J. Utilization of some non-coded amino acids as isosteres of peptide building blocks. *Amino Acids,* 1996;11(3–4);367–377;

Hutinec, A.; Ziogas, A.; Rieker, A. Non-natural phenolic amino acids. Synthesis and application in peptide chemistry. *Amino Acids*, 1996;11(3–4):345–366;

Meffre P.; Le Goffic F. β,γ-alkynyl α-amino acids. A synthetic challenge. *Amino Acids*, 1996;11(3–4):313–328;

Iyer M. S.; Gigstad, K. M.; Namdev, N. D.; Lipton, M. Asymmetric catalysis of the Strecker amino acid synthesis by a cyclic dipeptide. *Amino Acids*, 1996;11(3–4):259–268;

Easton, Christopher J. Free-Radical Reactions in the Synthesis of α-Amino Acids and Derivatives. *Chem. Rev.* (Washington, D. C.), 1997;97(1):53–82;

Chucholowski, Alexander; Masquelin, Thierry; Obrecht, Daniel; Stadlwieser, Josef; Villalgordo, Jose M. Novel solution- and solid-phase strategies for the parallel and combinatorial synthesis of low-molecular-weight compound libraries. *Chimia*, 1996;50(11):525–530;

Williams, Robert M. Asymmetric syntheses of α-amino acids. *Adv. Asymmetric Synth.*, 1995;1:45–94;

Sardina, F. Javier; Rapoport, Henry. Enantiospecific Synthesis of Heterocycles from α-Amino Acids. *Chem. Rev.* (Washington, D. C.), 1996;96(6):1825–1872;

Cardillo, Giuliana; Tomasini, Claudia. Asymmetric synthesis of β-amino acids and α-substituted α-amino acids. *Chem. Soc. Rev.*, 1996;25(2);117–128;

Studer, Armido. Amino acids and their derivatives as stoichiometric auxiliaries in asymmetric synthesis. *Synthesis*, 1996;(7):793–815;

Hruby, Victor J.; Qian, Xinhua. Approaches to the asymmetric synthesis of unusual amino acids. *Methods Mol. Biol.* (Totowa, N.J.), 1994;35(Peptide Synthesis Protocols):249–286;

Juaristi, Eusebio; Quintana, Delia; Escalante, Jaime. Enantioselective synthesis of β-amino acids. *Aldrichimica Acta*, 1994;27(1):3–11;

Cole, Derek C. Recent stereoselective synthetic approaches to β-amino acids. *Tetrahedron*, 1994;50(32):9517–9582;

Duthaler, Rudolf O. Recent developments in the stereoselective synthesis of α-amino acids. *Tetrahedron*, 1994;50(6):1539–1650;

Totah, Nancy I.; Schreiber, Stuart L. Asymmetric synthesis on carbohydrate templates: stereoselective Ugi synthesis of α-amino acid derivatives. *Chemtracts: Org. Chem.*, 1988;1(4):302–305;

Angst, Christof. Stereoselective synthesis of β,γ-unsaturated amino acids. *Pure Appl. Chem.*, 1987;59(3):373–380;

Schoellkopf, Ulrich. Asymmetric syntheses of amino acids via metalated bis-lactim ethers of 2,5-diketopiperazines. *Pure Appl. Chem.*, 1983;55(11):1799–1806;

Schoelkopf, Ulrich. Enantioselective synthesis of nonproteinogenic amino acids. *Top. Curr. Chem.*, 1983;109:65–84; and Steglich, W. Amino acids as synthesis materials and means for carbon-carbon bond formations. *Chimia*, 1978;32(10):394–395.

The synthesis of preferred compounds of Formula Ia is outlined in Schemes 3 and 4.

SCHEME 3

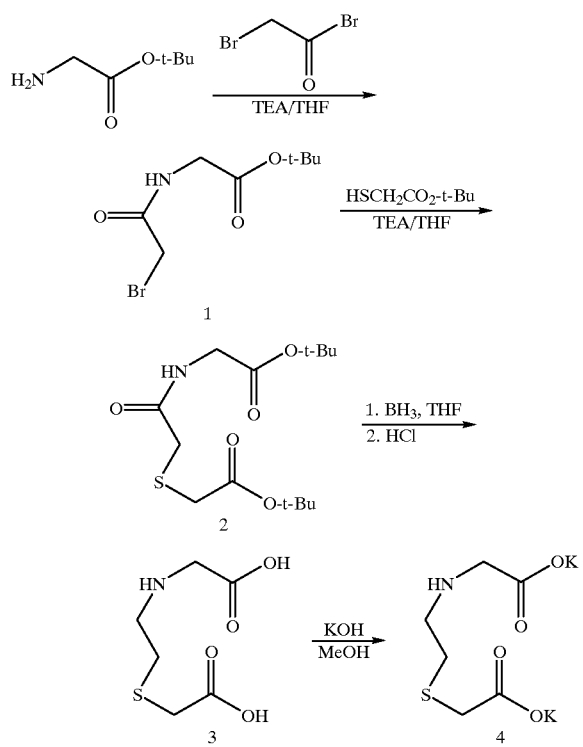

SCHEME 4

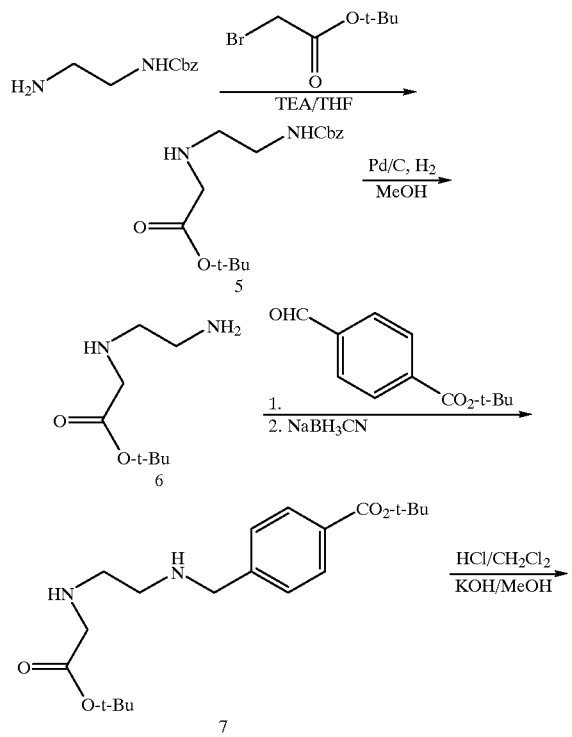

-continued

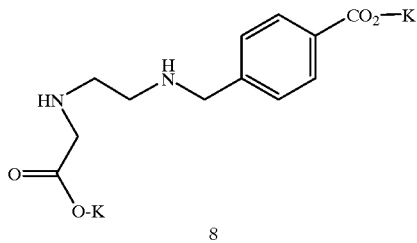

8

Thus, compound 4 ((2-Carboxymethylsulfanyl-ethylamino)-acetic acid dipotassium salt) is prepared as follows:

Acylation of the amino group of compound 2 (t-butyl glycinate) with an alkylating agent such as, for example, bromoacetyl bromide and the like in the presence of an organic base such as, for example, trialkylamine and the like, preferably triethylamine or an inorganic base such as, for example, sodium or potassium carbonate and the like in a polar solvent such as, for example, DMF, an ethereal solvent such as dioxane or THF, preferably THF, affords compound 1. The reaction is carried out at a temperature ranging from about room temperature to about 60° C. The product (compound 1) is isolated by normal aqueous workup using EtOAc or CHCl₃ as the extraction solvent and the product purified by column chromatography (SiO₂).

Subsequent alkylation of compound 1 with a bifunctional compound such as, for example, t-butyl mercaptoacetate or a homolog thereof, preferably t-butyl mercaptoacetate in the presence of an inorganic base such as, for example, potassium carbonate, sodium carbonate and the like or an organic base such as, for example, trialkylamine and the like, preferably triethylamine, affords compound 2. The reaction is carried out in an ethereal solvent such as, for example, THF, dioxane and the like, preferably THF. The product is isolated by aqueous workup using EtOAc or CHCl₃, preferably EtOAc as the extraction solvent.

Reduction of the amide functionality in compound 2 with concomitant hydrolysis of the t-butyl esters affords compound 3. The reduction is carried out with reducing agents such as, for example, boron hydrides and the like, preferably borane-methyl sulfide complex. The reaction is carried out in an ethereal solvent such as, for example, THF, dioxane and the like, preferably THF, at a temperature ranging from about room temperature to about reflux, preferably around 40° C. The product is worked up by warming the reaction mixture in aqueous HCl and isolating the product as a hydrochloride salt. The cleavage of the t-butyl esters occur during the acidic workup.

The acid derivative (compound 3) is suspended in a hydroxylated solvent such as, for example, methanol, ethanol and the like, and the base is added to it until the reaction mixture is neutral. The base is an inorganic base such as, for example, sodium, potassium hydroxide and the like, preferably potassium hydroxide in a methanolic solution. The product (compound 4) is purified by crystallization using mixed solvents such as, for example, aqueous acetone, aqueous methanol and the like.

The compound of Formula 8 (4-{[2-(Carboxymethyl-amino)-ethylamino]-methyl}-benzoic acid dipotassium salt) is prepared as follows:

Alkylation of N-Cbz ethylene diamine with a halo ester such as, for example, t-butyl bromoacetate affords compound 5. The reaction is carried out in the presence of an organic base such as, for example, triethylamine and the like using an ethereal solvent such as, for example, THF and the like. The product (compound 5) is purified by aqueous workup and purified by chromatography or crystallization.

Reductive deprotection of the N-Cbz group in compound 1 affords compound 6. The reaction is carried out under catalytic hydrogenation conditions using Pd/C as the catalyst at hydrogen pressure of up to 50 psi. The solvent used is an ethereal solvent such as, for example, THF or a hydroxylated solvent such as, for example, methanol and the like, preferably THF.

Formation of an imine by reaction with an appropriately substituted aldehyde derivative, preferably t-butyl 4-formylbenzoate, and the subsequent reduction of the imine to the corresponding amine affords compound 7. The initial reaction is carried out in the presence of a dehydrating agent such as, for example, MgSO₄, CaCl₂, molecular sieves and the like in a non-polar solvent such as, for example, benzene, toluene and the like, or a chlorinated solvent such as, for example, dichloromethane, chloroform and the like, preferably chloroform. Reaction is carried out at a temperature ranging from about room temperature to about reflux, preferably reflux. The product is isolated by filtration followed by evaporation of volatile impurities under vacuum. The imine is reduced by a borohydride reagent such as, for example, sodium cyanoborohydride or under catalytic hydrogenation conditions such as, for example, hydrogen pressure up to 50 psi and an activated catalyst such as Pd/C, preferably using sodium cyanoborohydride in a solvent such as, for example, methanol and the like. The product is isolated by crystallization or column chromatography over SiO₂.

Finally, deprotection of the t-butyl esters in compound 7 and formation of the potassium salt of the free carboxylic acid functionalities affords compound 8. The deprotection is carried out under acidic conditions using HCl in a solvent such as, for example, dichloromethane, dioxane and the like, preferably dichloromethane. The reaction mixture is worked up by evaporating the solvent and isolating the product as the hydrochloride. The potassium salt is prepared by treating the hydrochloride derivative with potassium hydroxide in a polar solvent such as, for example, methanol or water, preferably methanol. The product is isolated by evaporation of the solvent and recrystallization from methanol or acetone-water mixture.

Additionally, other compounds of Formula Ia can be prepared following the aforementioned procedures using different nucleophiles in place of t-butyl mercaptoacetate or using different aldehydes in place of t-butyl-4-formyl benzoate.

EXAMPLE 1

General Procedure for the Preparation of Ureas

Ureas were prepared by treating N-methylbenzylamine with isocyanate in THF and quenching with potassium sarcosinate followed by aqueous quench to afford the desired urea. A list of ureas prepared by this procedure is shown in Table 1.

TABLE 1

Synthesis of Ureas

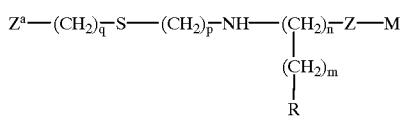

| Compound | R | Yield (%) | MS m/z |
|---|---|---|---|
| 1 | Et | >99 | 193 |
| 2 | n-Butyl | >99 | 221 |
| 3 | i-Propyl | >99 | 207 |
| 4 | t-Butyl | >99 | 221 |
| 5 | Benzyl | >99 | 255 |
| 6 | Cyclohexyl | >99 | 247 |
| 7 | Phenyl | >99 | 241 |
| 8 | 2-Et-phenyl | 98 | 269 |
| 9 | 2,6-Dimethyl-phenyl | 96 | 269 |
| 10 | 2-i-Pr-phenyl | >99 | 283 |
| 11 | 2,6-Diisopropyl-phenyl | 98 | 193 |
| 12 | 4-Chloro-phenyl | 93 | 275 |
| 13 | 4-Trifluoro-phenyl | 87 | 221 |
| 14 | 2-Nitro-phenyl | >99 | 286 |
| 15 | 4-Nitro-phenyl | >99 | 286 |
| 16 | 4-Carbethoxy-phenyl | >99 | 313 |
| 17 | 2-Methoxy-phenyl | >99 | 271 |
| 18 | $CH_2CO_2Et$ | 97 | 251 |

EXAMPLE 2

Procedure for the Preparation of Amides

Amides were prepared by treating N-benzylamine (0.302 g, 2.5 mmol) with an acid chloride (3.5 mmol) in DMF (2 mL) and triethylamine (0.695 g, 5 mmol). Reaction was quenched with potassium sarcosinate (0.127 g, 1 mmol) and water (6 mL). The product was isolated by filtration in the case of solids and with EtOAc (10 mL) in the case of oils. EtOAc extract was pipetted out rated to give the product. A list of amides prepared by this procedure is Table 2.

TABLE 2

Synthesis of Ureas

| Compound | R | Yield (%) | MS m/z |
|---|---|---|---|
| 1 | $CH_3$ | >99 | 164 |
| 2 | Benzyl | 98 | 240 |
| 3 | Cyclohexyl | 98 | 232 |
| 4 | Diphenylmethyl | 72 | 316 |
| 5 | $CH_2CH_2Ph$ | 92 | 254 |
| 6 | Phenyl | >99 | 226 |
| 7 | Piperonal | 85 | 270 |
| 8 | 3,4-Dichloro-phenyl | >99 | 294 |
| 9 | $4-NO_2—Ph$ | 81 | 271 |

EXAMPLE 3

Procedure for the Preparation of Sulfonamides

Sulfonamides were prepared by treating N-benzylamine (0.302 g, 2.5 mmol) with a sulfonyl chloride (3.5 mmol) in DMF (2 mL) and triethylamine 0.695 mmol). Reaction was quenched with potassium sarcosinate (0.127 g, 1 mmol) and water (6 mL). The product was isolated by filtration in the case of solids and extracted with EtOAc (10 mL) in the case of oils. EtOAc extract was out and evaporated to give the product. A list of sulfonamides prepared procedure is shown in Table 3.

TABLE 3

Synthesis of Sulfonamides

| Compound | R | Yield (%) | MS m/z |
|---|---|---|---|
| 1 | Benzyl | 91 | 276 |
| 2 | p-Tolyl | 79 | 276 |
| 3 | p-Methoxyphenyl | >99 | 296 |
| 4 | p-Chlorophenyl | >99 | 292 |
| 5 | 3,4-Difluorophenyl | >99 | 254 |
| 6 | 2,4,6-Triisopropyl phenyl | 75 | 388 |
| 7 | 1-Naphthyl | >99 | 312 |

What is claimed is:

1. A compound of formula Ia $$Z^a—(CH_2)_{\overline{q}}S—(CH_2)_{\overline{p}}NH—(CH_2)_{\overline{n}}Z—M$$
$$\underset{R}{\overset{|}{(CH_2)_m}}$$

wherein p is an integer of 2 to 6;

q is an integer of 1–6;

n is an integer from 1 to 10;

m is zero or an integer of from 1 to 6;

$Z^a$ is

—$CO_2R^4$, wherein $R^4$ is hydrogen, alkyl, or arylalkyl,

—$PO_3HR^4$, wherein $R^4$ is as defined above,

—$SO_2R^5$ wherein $R^5$ is hydroxy, alkoxy, arylalkoxy,

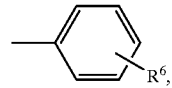

wherein
$R^6$ is
—$CO_2R^4$, wherein $R^4$ is as defined above,
—$PO_3HR^4$, wherein $R^4$ is as defined above, —SO₂R⁵, wherein R⁵ is as defined above, or

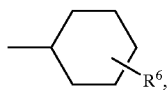

wherein R⁶ is as defined above;

R is
  hydrogen,
  alkyl,
  alkylenyl,
  alkynyl,
  cycloalkyl,
  aryl,
  heteroaryl,

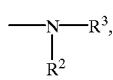

wherein
  R² and R³ are each the same or different and each is
    hydrogen,
    alkyl,
    cycloalkyl,
    aryl, or
    heteroaryl
—OR², wherein R² is as defined above,
—SR², wherein R² is as defined above,

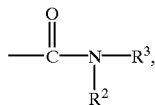

wherein R² and R³ are each the same or different and each is as defined above,

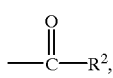

wherein R² is as defined above,

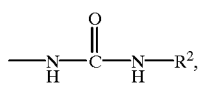

wherein R² is as defined above, or

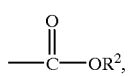

wherein R² is as defined above;

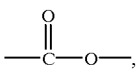

Z is

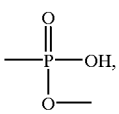

or

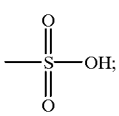

and
M is an alkali metal or alkaline earth metal.

2. A compound selected from the group consisting of:

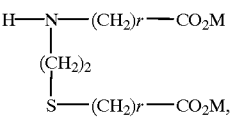

wherein r is an integer of from 1 to 4, and M is an alkali metal or alkaline earth metal;

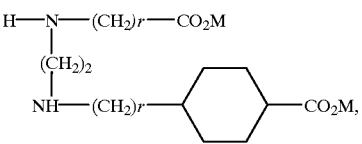

wherein r and M are as defined above; and

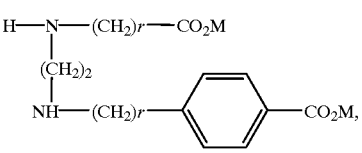

wherein r and M are as defined above.

3. A compound selected from the group consisting of:
(2-Carboxymethylsulfanyl-ethylamino)-acetic acid;
2-[2-(Carboxymethyl-amino)-ethylsulfanyl]-propionic acid;
4-[2-(Carboxymethyl-amino)-ethylsulfanyl]-butyric acid; and
5-[2(Carboxymethyl-amino)-ethylsulfanyl]-pentanoic acid.

* * * * *